(12) United States Patent
Jagiella et al.

(10) Patent No.: US 6,879,404 B2
(45) Date of Patent: Apr. 12, 2005

(54) DEVICE AND METHOD FOR CHECKING BORES IN OR EDGES ON AN OBJECT OF MEASUREMENT

(75) Inventors: Manfred Jagiella, Notzingen (DE); Sorin Fericean, Leonberg (DE)

(73) Assignee: Balluff GmbH, Neuhausen (DE)

(*) Notice: Subject to any disclaimer, the term of this patent is extended or adjusted under 35 U.S.C. 154(b) by 0 days.

(21) Appl. No.: 10/616,893

(22) Filed: Jul. 9, 2003

(65) Prior Publication Data

US 2004/0051520 A1 Mar. 18, 2004

Related U.S. Application Data

(63) Continuation-in-part of application No. 10/047,447, filed on Jan. 14, 2002.

(30) Foreign Application Priority Data

| Jan. 22, 2001 | (DE) | .......................................... 101 03 177 |
| Jul. 11, 2002 | (DE) | .......................................... 102 32 131 |

(51) Int. Cl.⁷ .............................................. G01B 11/14
(52) U.S. Cl. .................................... 356/614; 356/241.1
(58) Field of Search .......................... 356/237.1–237.6, 356/241.1–241.5, 614–623; 324/207.17; 451/5, 6; 901/9, 41; 318/568.22

(56) References Cited

U.S. PATENT DOCUMENTS

| 3,327,584 A | * | 6/1967 | Kissinger ..................... 356/614 |
| 4,199,258 A | * | 4/1980 | Dau ............................ 356/626 |
| 4,465,374 A | * | 8/1984 | Pryor et al. .................. 356/635 |

(Continued)

FOREIGN PATENT DOCUMENTS

| DE | 38 39 386 | 5/1990 |
| DE | 39 10 297 | 10/1990 |
| DE | 40 40 084 | 6/1992 |
| DE | 41 02 721 | 8/1992 |
| DE | 42 17 292 | 12/1993 |
| DE | 42 31 989 | 1/1994 |
| DE | 42 32 837 | 3/1994 |
| DE | 196 24 233 | 10/1997 |
| DE | 198 47 365 | 5/2000 |
| DE | 198 53 302 | 5/2000 |
| EP | 0 557 558 | 9/1993 |
| GB | 794985 | 5/1958 |
| JP | 363058134 A | * 3/1988 |

OTHER PUBLICATIONS

*Patent Abstracts of Japan*, Abstract of Japanese Patent "Burr Removing Robot Control Method", Publication No. 04310360, Nov. 2, 1992, Japanese Application No. 03072794, Filed Apr. 5, 1991.

*Patent Abstracts of Japan*, Abstract of Japanese Patent "Method and Device of Detecting Casting Skin Surface Around Burr in Casting Burr Removing Work", Publication No. 63174857, Jul. 19, 1988, Japanese Application No. 62008545, Filed Jan. 16, 1987.

*Patent Abstracts of Japan*, Abstract of Japanese Patent "Method for Measuring Burr Shape and Dimensions Generated on Plate Shear", Publication No. 06066536, Mar. 8, 1994, Japanese Application No. 04245804, Filed Aug. 21, 1992.

(Continued)

*Primary Examiner*—Hoa Q. Pham
(74) *Attorney, Agent, or Firm*—Barry R. Lipsitz; Douglas M. McAllister (57) ABSTRACT

A method for checking bores in or edges on an object of measurement, and in particular for recognizing burrs. A prepared object of reference is scanned with a distance sensor in correlation with scanning the prepared object of reference with another distance sensor. The measurement signals of the two distance sensors are then compared.

28 Claims, 3 Drawing Sheets

U.S. PATENT DOCUMENTS

| | | | |
|---|---|---|---|
| 4,942,672 A | | 7/1990 | Yoshida |
| 4,967,092 A | * | 10/1990 | Fraignier et al. ...... 250/559.07 |
| 5,243,265 A | * | 9/1993 | Matsuura et al. ........... 318/578 |
| 5,302,894 A | | 4/1994 | Hrubes |
| 5,473,156 A | * | 12/1995 | Pinnock et al. ........ 250/227.11 |
| 5,485,082 A | * | 1/1996 | Wisspeintner et al. ...... 324/202 |
| 5,942,693 A | | 8/1999 | Harms et al. |
| 6,155,757 A | * | 12/2000 | Neumann ................... 409/131 |
| 6,628,408 B1 | * | 9/2003 | Franklin et al. ............. 356/623 |
| 2004/0136010 A1 | * | 7/2004 | Jensen et al. ............... 356/601 |

OTHER PUBLICATIONS

*Patent Abstracts of Japan*, Abstract of Japanese Patent "Automatic Shape Tolerance Measuring Method and its Measuring Instrument", Publication No. 61111410, May 29, 1986, Japanese Application No. 59232367, Filed Nov. 6, 1984.

Extract from Delphion database relating to *JP 2051001*, "Method and Device for Measuring Height of Burr", Issued Feb. 21, 1990, Japanese Application No. 1988000200034, Filed Aug. 12, 1988.

Extract from Delphion database relating to *JP 11153414*, "Measuring Method of Burr Height and Mold Deviation of Molding", Issued Jun. 8, 1999, Japanese Application No. 1997000362423, Filed Nov. 21, 1997.

* cited by examiner

FIG.5 understand# DEVICE AND METHOD FOR CHECKING BORES IN OR EDGES ON AN OBJECT OF MEASUREMENT The present disclosure relates to the subject matter disclosed in German patent application No. 102 32 131.0 of Jul. 11, 2002, which is incorporated herein by reference in its entirety and for all purposes.

BACKGROUND OF THE INVENTION

The invention relates to a device and a method for checking bores or edges and, in particular, for recognizing burrs in or on an object of measurement.

Burrs can occur where workpieces are machined and chips are thereby removed from the material of the workpieces. For example, burrs can occur on bores or edges. Burrs can cause a disturbance for a number of reasons. There should, for example, be no burrs at interfaces which are to be sealed as this would influence the sealing effect. It may be desirable for there to be no projection of material on workpieces. The presence of burrs which drop off during component assembly can be a nuisance. If they fall off during operation of a unit, this can destroy it. Burrs at the edges of the material of a workpiece to be coated can result in irregular paint densities. Sharp-edged burrs on outer workpiece surfaces can cause injury due to cuts.

It is, therefore, often necessary to make a check for burrs after the machining of the workpiece, and this may involve two aspects, namely a qualitative burr check as to whether burrs are present and a quantitative check as to whether, for example, a certain tolerance for the height of a burr is exceeded.

A sensor device for checking burrs, which is universally employable in a simple way, is described in German patent application No. 101 03 177.7, which corresponds to the U.S. patent application Ser. No. 047,447 on Jan. 14, 2002 and belongs to the applicant of the present application. These patent applications are not previously published.

SUMMARY OF THE INVENTION

In accordance with the present invention, a device for checking bores in or edges on an object of measurement, in particular, for recognizing burrs, which can be used in a simple way, is provided.

This is accomplished in accordance with the invention by a first distance sensor with a detector head being provided, the detector head being positionable at a distance from the object of measurement and detector head and object of measurement being movable relative to one another, the detector head coupling electromagnetically with the object of measurement or the object of measurement being able to be acted upon with an electromagnetic signal by the detector head, and the coupling with the object of measurement or an electromagnetic reaction signal of the object of measurement to the signal acting upon it being a function of a distance between detector head and object of measurement so that this distance is determinable in a contact-free manner, and a surface of the object of measurement being scannable by the detector head in a contact-free manner, a second distance sensor with a detector head also being provided, by means of which an object of reference is scannable in correlation with the first distance sensor, and a comparator being provided for comparing the measurement signals of the first distance sensor and the second distance sensor so that the object of measurement is characterizable in relation to the object of reference.

Owing to the inventive use of a distance sensor as a separate component, with this distance sensor interacting with the workpiece and the interaction depending on the distance between distance sensor and workpiece, a surface examination of a bore or edge, in particular, as burr check, can be carried out in a simple way. The distance sensor forms a sensor field which couples locally with the workpiece. As a result, inner workpiece surfaces (i.e., also bore surfaces) can also be checked when the distance sensor is inserted accordingly into the workpiece. The checking is carried out without any contact being made and so simple and, in particular, also mechanical use is enabled.

Owing to the object of measurement and an object of reference being scanned in a correlated manner, a deviation between object of measurement and object of reference can be deduced in a simple way, for example, from a difference between measurement signals of the two distance sensors. If the object of reference is ideally prepared, a difference then means that the object of measurement contains a flaw. It can then be determined from the height of the differential signal, for example, whether the object of measurement is still usable or has to be eliminated from the production process, i.e., lies beyond a tolerance range.

With the inventive device, a quick and simple examination of objects of measurement can be carried out, for example, in series production, and automation of this examination with respect to the evaluation is also possible.

Aside from burrs, other deviations in relation to the prepared bores in the object of reference are also recognizable, for example, deviations in shape or deviations in dimension.

In particular, provision is made for the first distance sensor and the second distance sensor to be of essentially the same design so as to enable a simple comparison to be made between object of measurement and object of reference.

Further provision is made for first distance sensor and second distance sensor to be coupled to one another in a fixed distance relationship and/or angular relationship during a checking procedure. For example, for linear displacement of the second distance sensor with respect to the object of reference there should be a rigid coupling with the first distance sensor. A correlated or synchronized movement of the two distance sensors is thereby automatically ensured. If a rotational movement of the second distance sensor relative to the object of reference is carried out, then a rotational movement of the first distance sensor relative to the object of measurement should also be correlated with the first aforementioned rotational movement.

A guide device is advantageously provided for guidance of the second distance sensor relative to the object of reference in a defined manner, and, in particular, for linearly displaced guidance thereof relative to the object of reference and/or for rotation relative thereto. Depending on the use, the guide device may be designed such that a linear displacement is permitted only in one direction, only in one plane or in all three spatial directions.

In particular, the first distance sensor then follows the guidance of the second distance sensor so that the object of measurement is scannable in a guided manner.

It is particularly advantageous for the object of reference to be prepared so that it represents the ideal case, and any deviation from the object of reference constitutes the detection result.

In particular, the comparator forms a differential signal for the measurement signals of the first distance sensor and the second distance sensor. A direct comparison can thus be made in a simple way so as to be able to characterize the measurement result on the object of measurement relative to the object of reference. If the differential signal has an immeasurably small value this means that there are no differences between object of measurement and object of reference in the measured range. If the differential signal has a finite value, then corresponding differences were detected. Conclusions can then also be drawn about the origin of this difference from the absolute value of the differential signal, for example, whether it is a burr and what type of burr it is.

In particular, provision is then made for the comparator to comprise a threshold value switch for inhibiting noise signals and the like with respect to formation of the difference or for rejecting signals below a tolerance threshold as insignificant.

It is particularly expedient for the first distance sensor and the second distance sensor or a first distance sensor combination and a second distance sensor combination, which comprise the first distance sensor and the second distance sensor, respectively, and at least one further distance sensor, and with which the object of measurement and the object of reference, respectively, is scannable, to comprise a plurality of areas of sight. Via this plurality of areas of sight, an alignment and, in particular, a coaxial alignment of a distance sensor or a distance sensor combination in a bore can, for example, be checked, and, where necessary, readjusted. Moreover, such a plurality of areas of sight is suitable for enabling exact characterization, in particular, with respect to absolute evaluation. Furthermore, a larger surface area can be simultaneously scanned, with the result that a checking procedure can be carried out faster.

It is advantageous for an area of sight, in particular, of the first distance sensor or the first distance sensor combination to be arranged so as to point in a direction in which the distance sensor or distance sensor combination is displaceable towards the object of measurement. As a result, a warning signal can be generated if there is a danger of collision with the object of measurement, and this can be thereby avoided. Such dangers of collision exist, for example, if a bore is not drilled to a sufficient depth.

Furthermore, it is expedient for areas of sight to be arranged such that the same surface area of the object of measurement and the object of reference is scannable upon linear movement of the first distance sensor and the second distance sensor, respectively, or of the first distance sensor combination and the second distance sensor combination, respectively. If the areas of sight are of different configuration, for example, with respect to the electromagnetic coupling to the corresponding object, an absolute statement can then also be made regarding the distance from the object of measurement and the object of reference, respectively, by way of the respective area of sight and the measurement signals associated therewith, and, in particular, when a difference is formed.

Provision may also be made for areas of sight to be arranged such that an identical surface area of the object of measurement and the object of reference, respectively, is scannable upon rotational movement of the first and the second distance sensor, respectively, or the first and the second distance sensor combination, respectively. This covers the special case where areas of sight face opposite surfaces of a bore. With corresponding measurement signals associated with the areas of sight, an alignment of a distance sensor or a distance sensor combination within a bore can then be carried out so as to achieve, for example, an ideal coaxial guidance with a high degree of precision.

Provision may be made for one or several areas of sight to be externally or internally selectable for optimum adaptation of the measurement to a use.

It is particularly advantageous for a distance sensor or a combination of several distance sensors to be designed as a probe which is insertable into a bore. Such a bore can thereby be scanned so to able to check the bore, in particular, for burrs.

In practice, it is of importance for object of measurement and object of reference to be made of a metallic material. Engine blocks, for example, which have a large number of bores, are a typical example of use.

It is advantageous for the first and the second distance sensor to be an inductive sensor which couples inductively with the object of measurement and the object of reference, respectively. Such an inductive sensor couples electromagnetically with a metallic material. This enables advantageous measurement of distances from a workpiece, and a measurement is insensitive to contaminations such as oil, as the inductive coupling remains substantially uninfluenced thereby insofar as the contamination is non-metallic.

To provide a plurality of areas of sight on a sensor, an inductive sensor advantageously comprises a plurality of coils. A coil then supplies a corresponding measurement signal, and quantitative statements regarding distances can then be determined with a high degree of accuracy, for example, from the difference between such measurement signals of various coils. This difference evaluation can be carried out internally in the inductive sensor.

A further object underlying the invention is to provide a method for checking bores in or edges on an object of measurement, and, in particular, for recognizing burrs, which enables bores to be checked in a simple and accurate way.

This object is accomplished in accordance with the invention by a prepared object of reference being scanned by a distance sensor and by the object of measurement then being scanned in correlation therewith by a further distance sensor and by a comparison being made of the measurement signals of the two distance sensors.

The inventive method has the advantages set forth hereinabove in conjunction with the inventive device.

Further advantageous embodiments have also been explained hereinabove in conjunction with the inventive device.

The following description of preferred embodiments serves to explain the invention in greater detail in conjunction with the drawings.

DETAILED DESCRIPTION OF THE INVENTION

When a workpiece and, in particular, a metallic workpiece is machined with a chip-removing tool, in particular, a metal-cutting tool, burrs can form on outer and inner surfaces, such as bore intersections, or at edges of the workpiece. This is shown schematically in FIGS. 1a to c for bores.

Figure 1A:
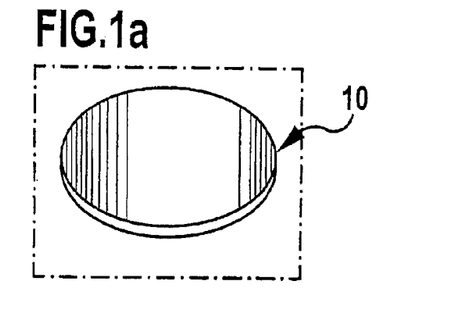
FIGS. 1a, 1b, 1c show various burr formations on a bore in a workpiece.

One differentiates between various types of burr: The so-called burr of burr type 1, generally designated 10 in FIG. 1a, is formed as a simple burr in the shape of a circumferential edge elevation, with the height of the burr exceeding 0.15 mm. A burr of burr type 2 is also a simple burr with a burr height of approximately 1.1 mm.

Figure 1B:
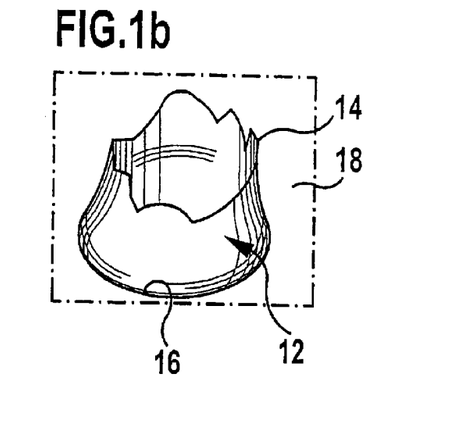
Figure 1C:
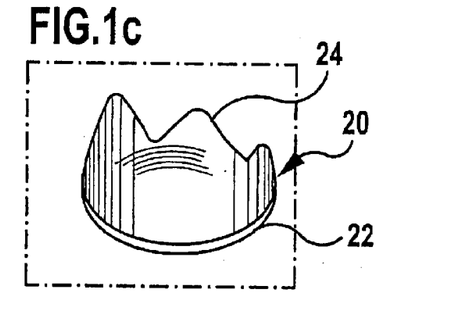

A burr of burr type 3, generally designated 12 in FIG. 1b, is also referred to as a crown burr because a circumferential edge 14 of this burr is of jagged configuration. The height of the burr of burr type 3 is approximately 0.65 times the diameter of the bore 16 in the workpiece 18, on which the burr is formed.

A burr of burr type 4 is a simple burr having a bore cap suspended from the workpiece (not shown in the drawings). In a burr of burr type 5, generally designated 20 in FIG. 1c, the circumferential edge 22 is very irregular in its height and protuberances 24 are formed, but—in contrast to the burr of burr type 3—these are not distributed around the entire edge 22 of the burr 20.

In accordance with the invention, a device for checking bores and workpieces, in particular, their edges, is provided (FIG. 5), with which it is possible to detect whether a burr is actually formed on a surface of an object of measurement. In particular, quantitative statements regarding a burr are also obtainable with the inventive device, for example, what dimensions it has or what type of burr it is. By corresponding measurement of the object of measurement various important items of information are then obtainable for the further processing of the object, such as, for example, whether subsequent machining is required for removal of a burr or reduction of the size of a burr. With a series of workpieces, examination of a tool may also be carried out by the change in the burr within the series of workpieces being monitored over time: For example, the blunting of a drilling tool may be determined from the type of burr formation on bore edges.

Furthermore, bores can be checked with respect to their dimensions or edges with respect to their accuracy.

Figure 2:
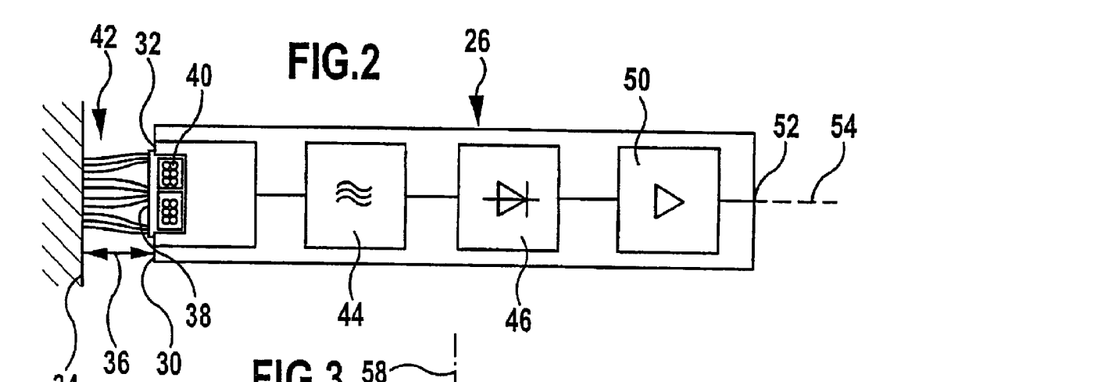
FIG. 2 shows a schematic illustration of an inductive distance sensor used in the inventive device for checking bores.

FIG. 2 shows schematically an embodiment of a first distance sensor, generally designated 26 therein, comprising a detector head 30. The detector head 30 has an active surface 32, via which it can electromagnetically couple with a workpiece 34 as object of measurement. The coupling is determined by a distance 36 between the active surface 32 of the detector head 30 and the workpiece 34.

In the embodiment shown in FIG. 2, the distance sensor 26 is an inductive proximity sensor which inductively couples via the generation of eddy currents with the workpiece 34, which, to this end, must be made of a metallic material. For this purpose, the detector head 30 of the distance sensor 26 has a coil 38 facing the active surface 32 as inductive element, with which the metallic workpiece 34 inductively couples.

In the embodiment shown, the coil 38 is provided with a pot core 40. A base area of the pot core 40 essentially defines the active surface 32. The area of a pot core cap 41 corresponds approximately to the active surface 32. A sensing area 42 of the distance sensor 26 lies in front of the active surface 32.

The distance sensor 26 also comprises, for example, an oscillator 44, a demodulator 46 and an output driver 50. An analog output signal is made available at an output 52 of the distance sensor 26, for example, a voltage signal which is a function of the distance between the active surface 32 of the detector head 30 and the workpiece 34.

Alternatively, provision may be made for a coil 38 of the distance sensor 26 to be without a core. For example, a metallic workpiece 34 influences the amplitude of the oscillating oscillator 44 by inductive coupling, and the amplitude and/or frequency and/or phase of the oscillator 44 is a measure of the distance 36.

The interaction of the distance sensor 26 occurs only via the active surface 32 which in its configuration and positioning relative to the workpiece defines the sensing area 42. The distance sensor 26 with its detector head 30 can be positioned locally on the workpiece 34 and interaction then occurs locally between the detector head 30 and the workpiece 34 owing to a local sensor field. If there is a burr in the sensor field 42, the electromagnetic (inductive) coupling between the active surface 32 and the workpiece 34 is thereby influenced, and the output signal 52 changes accordingly. Local information about the workpiece is thereby obtained, namely whether a burr is present, if the signal changes accordingly, and quantitative information about the burr is, in turn, obtainable from the change in the signal itself.

The distance sensor 26 in FIG. 2 has been described by way of example as an inductive distance sensor which couples inductively with the workpiece. Provision may, however, also be made for the distance sensor to be a capacitive distance sensor which couples capacitively with the workpiece 34. Here, too, the coupling is an electromagnetic coupling, and again this electrostatic coupling is influenced by the distance 36. In this case, as well, a burr check may be carried out on the workpiece 34 from an output signal of a corresponding capacitive distance sensor.

In the embodiment shown in FIG. 2, the active surface 32 is formed symmetrically around a longitudinal axis 54 of the distance sensor 26. The sensor field 42 is then also formed symmetrically around this longitudinal axis 54 insofar as no coupled workpiece 34 is present, and when a workpiece 34 is coupled, this is also symmetrical in relation to the longitudinal axis 54 of a distance sensor 26 positioned at a distance, at least in the area of the effective sensing area 42.

An effective sensing area of the distance sensor 26 (the sensor field 42) therefore has an area of sight with a direction of sight which is essentially parallel to the longitudinal direction 54 of the distance sensor 26.

Figure 3:
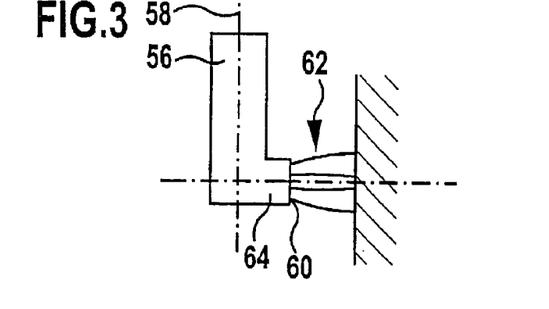
FIG. 3 shows a schematic illustration of a distance sensor with its area of sight in relation to a workpiece surface.

Provision may also be made, as shown schematically in FIG. 3, with a distance sensor 56 with a longitudinal direction 58, for an active surface 60 to be oriented transversely to this longitudinal direction 58 such that a corresponding area of sight defined by a sensor field 62 has a direction of sight 64 which is oriented essentially transversely and, in particular, at right angles to the longitudinal direction 58 of the distance sensor 56.

The area of sight of a distance sensor may be adjusted in a defined manner, and, in particular, restricted by screening elements in order, for example, to thereby achieve a high local resolution. Screening elements arranged accordingly influence the formation of the sensor field between the distance sensor and the workpiece. In the case of an inductive distance sensor, these may, in particular, be screening elements which influence the induction of eddy currents in the metallic workpiece 34 or, in the case of a capacitive distance sensor, these may be screening elements which influence the formation of the electric field between an active surface and the workpiece.

At the output 52 there is an analog output signal containing the distance information for the distance between detector head 30 and workpiece 34. Preferably, a separate evaluation unit to which this signal of a measuring head is transmitted cordlessly or through a line (not shown in the drawings) is also provided. The evaluation unit then determines from the burr information indirectly contained in the signal, by means of an evaluation algorithm, direct information about the burr formation, namely, in particular, about location and extent. For example, a comparison with a reference signal, corresponding to the burr-free workpiece at the same sensor position, is made for this purpose.

A distance sensor may also be an optical distance sensor, such as, for example, a light scanner. Such an optical distance sensor is described in German patent application No. 101 03 177.7, filed on Jan. 22, 2001, which corresponds to the U.S. patent application Ser. No. 047,447 on Jan. 14, 2002 and belongs to the applicant of the present application. Reference is hereby made explicitly to the content of these patent applications, which are not previously published.

An embodiment of an inventive device for checking bores 66 of an object of measurement 68 (FIG. 4), which, in particular, is metallic, comprises a first distance sensor 70, as described, for example, hereinabove with reference to FIG. 2, and designated 26 therein. This first distance sensor 70 is, for example, probe-shaped so that it can be inserted into a bore 66.

Figure 4:
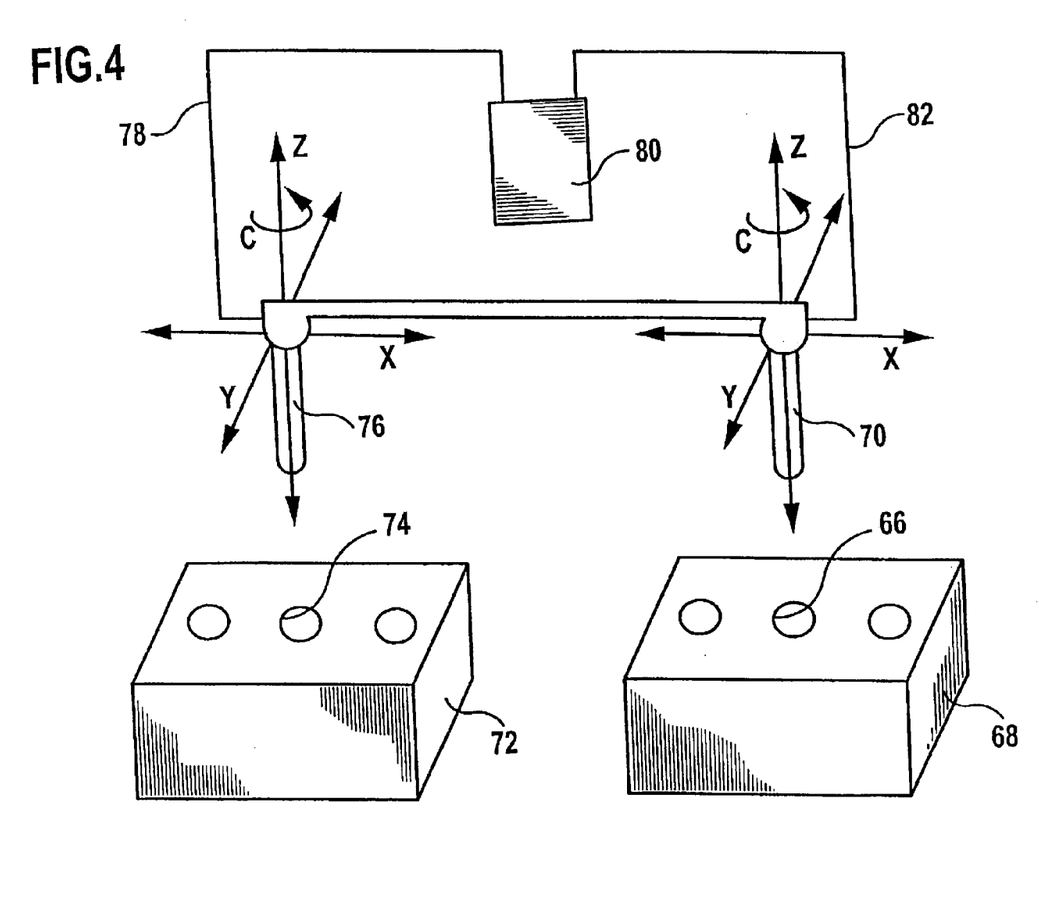
FIG. 4 shows an embodiment of an inventive device for checking bores.

An object of reference 72 prepared so as to correspond to an ideal workpiece is provided for checking such a bore 66. Accordingly, if the object of reference 72 and the object of measurement 68 exhibit no deviations in their characteristics, the object of measurement 68 with its bores 66 then fulfills all the requirements to be met by it.

The object of reference 72 has identically arranged bores 74 corresponding to bores 66, but these are prepared so as to be ideal and, in particular, free from burrs.

The inventive device for checking the bores 66 of the object of measurement 68 then comprises (at least) one second distance sensor 76 which is of the same design as the first distance sensor 70. This second distance sensor 76 can be inserted into the bores 74 of the object of reference 72 in order to measure the corresponding surfaces of the object of reference 72.

The two distance sensors 70 and 76 are coupled to one another in such a way that when the bore 74 is scanned by the second distance sensor 76, the bore 66 of the object of measurement 68 is correspondingly scanned.

If, for example, the second distance sensor 76 is displaced linearly in the bore 74, the first distance sensor 70 is then rigidly coupled to the second distance sensor 76 in such a way as to be guided in the bore 66 of the object of measurement 68 associated with it in correlation or synchronization with the guidance of the second distance sensor 76 relative to the bore 74 of the object of reference 72. The guidance is carried out by a guide device in the direction of the X- and/or Y- and/or Z-axes (the guide device is not shown in the drawings).

Provision may also be made, when the second distance sensor 76 is turned in the bore 74, for the first distance sensor 70 to also be turned with angular synchronization in the bore 66 of the object of measurement 68, so that, in principle, it is always the same relative surface area that is scanned by the two distance sensors 70 and 76, with the second distance sensor 76 scanning the object of reference 72 and the first distance sensor 70 scanning the object of measurement 68.

A measurement signal of the second distance sensor 76 is transmitted through a line 78 or cordlessly to a comparator 80. The measurement signal of the first distance sensor 70 is transmitted to this comparator 80 through a line 82 or cordlessly. The comparator 80 can then compare the incoming measurement signals of the two distance sensors 70 and 76 with one another, and, in particular, generate a differential signal and, where required, a summation signal. One can then read off from the differential signal whether there is a difference between the object of measurement 68 and the object of reference 72. As the object of reference 72 is usually prepared so as to be ideal, this difference then originates from deviations of the object of measurement 68 from the ideal case. These deviations are due, in particular, to burrs in the bores 66. Differences in the dimensions of the bores 66 or unmade transverse bores and the like may also be the cause.

The comparator 80 comprises, for example, a threshold value switch for eliminating noise signals in connection with the difference measurement or for excluding differential signals below a tolerance threshold, so that when the threshold value in the differential signal is exceeded, it can be assumed that there is a significant difference between object of measurement 68 and object of reference 72, i.e., there is a significant difference between bores 74 and 66.

Moreover, the type of deviation can then be concluded from the signal shape of, for example, the differential signal or a summation signal. For example, the presence of a burr can be concluded and the type of burr recognized, or a deviation in the dimensions can be concluded.

The two distance sensors 70 and 76 are guided in a correlated and, in particular, synchronized manner with respect to their respective workpieces by the guide device not shown in the drawings. Where workpieces are produced in series, only one object of reference 72 need be provided for checking a multiplicity of objects of measurement 68.

In principle, the guide device is designed such that insertion into corresponding bores of the object of measurement and the object of reference is possible in all spatial directions. As described hereinabove, provision is preferably also made for rotation of the second distance sensor 76 relative to the bore 74 and of the first distance sensor 70 relative to the bore 76 to be possible with angular correlation.

In particular, the inventive device may also comprise further distance sensors of substantially the same design so as to be able to simultaneously examine a plurality of bores 66 in the object of measurement 68, in particular, when these are arranged in parallel.

Figure 5:
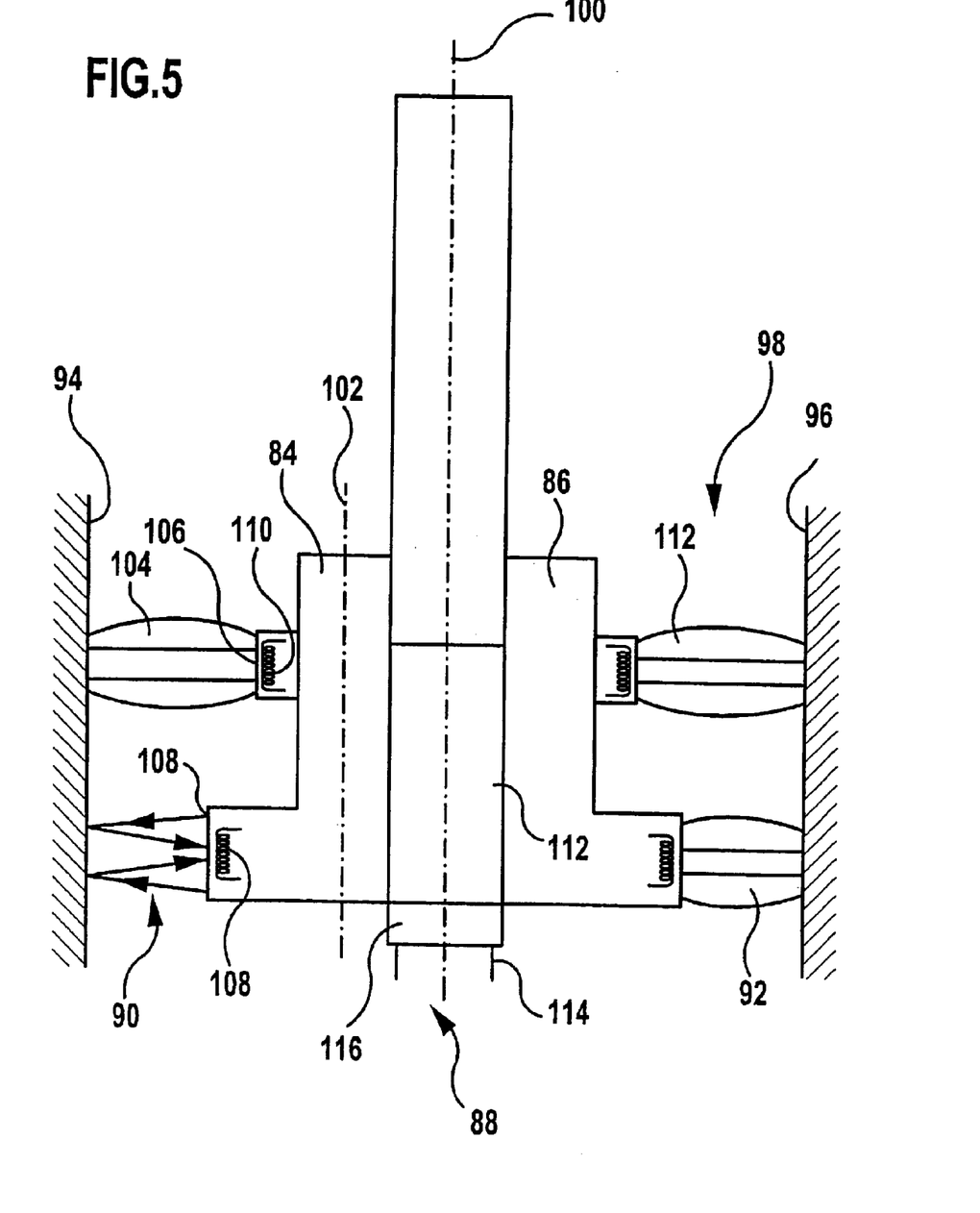
FIG. 5 shows an embodiment for a sensor assembly for checking a bore.

Provision may also be made, as shown schematically in FIG. 5, for several distance sensors 84, 86 to be combined into a distance sensor combination 88 which is inserted into a bore 66 and 74, respectively. A first distance sensor combination is then provided for measuring the object of reference 72, and a second distance sensor combination is provided for measuring the object of measurement 68.

At least two distance sensors 84, 86 having different areas of sight 90, 92 are provided in such a distance sensor combination 88. In particular, these areas of sight 90, 92 do not overlap, and, for example, face opposite surfaces areas 94, 96 of a bore. When such a distance sensor combination 88 is rotated in the bore, in a certain rotational position the area of sight 90 then scans a surface area which has previously been scanned by the area of sight 92.

The alignment of the distance sensor combination 88 within a bore 98 can be optimized by the provision of at least two areas of sight 90, 92. In particular, the distance sensor combination 88 can then be aligned coaxially with an axis of symmetry 100 of a cylindrical bore 98. In turn, the accuracy with which the distance sensor combination 88 is guided in the bore 98 is thereby improved.

In particular, a control circuit relating to the object of reference 72 can thus be formed to ensure that the second distance sensor combination 88 for scanning the bore 74 of the object of reference 72 is guided exactly coaxially with the corresponding axis 100 of this bore 74. For example, a differential signal is formed from the signals associated with the two areas of sight, and a finite value is then indicative of a deviation from the coaxial guidance. If the first distance sensor combination for scanning the bore 66 of the object of measurement 68 is guided in synchronization with the second distance sensor combination and, in particular, is rigidly guided relative thereto, the presence of, in particular, burrs can then be concluded from differences between the areas of sight 90 and 92, insofar as no such differences with respect to the second distance sensor combination in the bore 74 of the object of reference 72 exist.

Alternatively or additionally, provision may be made for a distance sensor 26 itself to have a plurality of areas of sight, for example, for the distance sensor 84 shown in FIG. 5 to have the area of sight 90 and an area of sight 104 offset in the longitudinal direction 102, with, for example, a smaller distance of a detector head 106 from the longitudinal direction 102 than a detector head 108 providing the area of sight 90.

In the embodiment shown, the distance sensor 84, if it is an inductive sensor, then comprises a first coil 108 for creating the area of sight 90 and a second coil 110 for creating the area of sight 104.

The distance from the bore surface 94 can then be determined from different measurement signals relating to the two areas of sight 90 and 104, which are detected within the sensor 84, by a differential signal being formed accordingly. A highly precise guidance of a single distance sensor 84 or a distance sensor combination 88 within a bore 98 is also achievable in this way.

The distance sensor 86 may also comprise a further area of sight 112.

When the distance sensor 84 is moved linearly in the direction 100 within the bore 98, the area of sight 104 then scans a surface area of the bore which had previously been scanned by the area of sight 90 or vice versa, depending on the direction of movement of the distance sensor 84 within the bore 98.

Provision is preferably made for areas of sight, for example, areas of sight 90, 92, 104, 112 to be able to be added on or omitted as required. This can be done externally through the operator or by an external evaluation device or internally by a corresponding sensor circuit. The inventive device can thereby be optimally adapted to a particular use by adjustment of the area of sight.

A further distance sensor 112 having an area of sight 114 on a detector head 116 pointing in the direction of a direction of movement of the combination 88 may also be provided. In particular, the first distance sensor or the first distance sensor combination is provided with such an area of sight 114. Thus, if there is a danger of collision with the object of measurement 68, a warning signal can be emitted (when the detector head 116 detects proximity to a wall), in order to discontinue further movement. A collision owing, for example, to insufficient depth of the bores on the object of measurement is thereby avoided.

In accordance with the invention, examination of a bore 66 in the object of measurement 68 (or an edge of the object of measurement 68) and, in particular, a check for a burr, is carried out by the object of reference 72 being previously prepared and object of measurement 68 and object of reference 72 then being held at a fixed distance from one another. The second distance sensor is positioned at a distance from the object of reference 72, and the first distance sensor 70 is thereby simultaneously positioned at a certain distance from the object of measurement 68. A local sensor field forms between the second distance sensor 76 with its detector head 30 with an active surface and the object of reference 72. The same applies accordingly to the first distance sensor 70 and the object of measurement 68. The distance of the detector head of the second and first distance sensors 76 and 70, respectively, from the object of reference 72 and the object of measurement 68, respectively, can be detected via this sensor field. In accordance with the invention, however, there is no need for absolute determination of the distance as the differential signal between the first distance sensor 70 and the second distance sensor 76 is evaluated.

An equivalent surface area of a bore 74 and 66, respectively, of the object of reference 72 and the object of measurement 68, respectively, is scanned by the correlated movement of the detector heads of the two distance sensors 76 and 70. A finite differential signal above a threshold indicates a difference, and as the object of reference 72 has been ideally prepared, this difference is due to deviations of the bore 66 in the object of measurement 68 from an ideal shape. These deviations can, in turn, be caused by, for example, burrs which have been correspondingly detected by the first distance sensor 70.

The comparison of the measurement signals of the two distance sensors 70 and 76 can be converted by the inventive device into a relative measurement without absolute measurement signals having to be evaluated in detail. (If, however, in addition to recognition of a burr or recognition of a deviation, quantitative statements regarding the origin of the deviation are to be made, then such a quantitative evaluation of the differential signal is required.)

The second distance sensor 76 scans the object of reference 72 locally, and the first distance sensor 70 scans the object of measurement 68 locally.

Further details are given in German patent application No. 101 03 177.7, filed on Jan. 22, 2001, which corresponds to the U.S. patent application Ser. No. 047,447 on Jan. 14, 2002 and belongs to the applicant of the present application. Reference is hereby made explicitly to the content of these patent applications, which are not previously published.

What is claimed is:

1. Device for checking bores in or edges on an object of measurement, comprising:

a first distance sensor for checking bores in or edges on said object of measurement with a detector head positionable at a distance from the object of measurement, detector head and object of measurement being movable relative to one another;

wherein the detector head couples electromagnetically with the object of measurement or the object of measurement is able to be acted upon with an electromagnetic signal by the detector head, and the coupling with the object of measurement or an electromagnetic reaction signal of the object of measurement to the signal acting upon it is dependent upon a distance between detector head and object of measurement so that this distance is determinable in a contact-free manner, and a surface of the object of measurement is scannable by the detector head in a contact-free manner;

a second distance sensor by means of which an object of reference is scannable in correlation with the first distance sensor; and a comparator for comparing the measurement signals of the first distance sensor and the second distance sensor so that the object of measurement is characterizable in relation to the object of reference.

2. Device in accordance with claim 1, wherein the first distance sensor and the second distance sensor are of essentially the same design.

3. Device in accordance with claim 1, wherein first distance sensor and second distance sensor are coupled to one another in a fixed distance relationship or a fixed angular relationship or in both a fixed distance relationship and a fixed angular relationship during a checking procedure.

4. Device in accordance with claim 1, wherein a guide device is provided for guiding the second distance sensor relative to the object of reference in a defined manner.

5. Device in accordance with claim 4, wherein the first distance sensor follows the guidance of the second distance sensor so that the object of measurement is scannable in a guided manner.

6. Device in accordance with claim 1, wherein the object of reference is prepared.

7. Device in accordance with claim 1, wherein the comparator forms a differential signal for the measurement signals of the first distance sensor and the second distance sensor.

8. Device in accordance with claim 7, wherein the comparator comprises a threshold value switch.

9. Device in accordance with claim 1, wherein the first distance sensor or a first distance sensor combination comprising the first distance sensor and at least one further distance sensor for scanning the object of measurement comprises a plurality of areas of sight.

10. Device in accordance with claim 9, wherein the areas of sight are arranged such that an identical surface area of the object of measurement is scannable upon linear movement of the first distance sensor or the first distance sensor combination.

11. Device in accordance with claim 9, wherein areas of sight are arranged such that an identical surface area of the object of measurement is scannable upon rotational movement of the first distance sensor or the first distance sensor combination.

12. Device in accordance with claim 9, wherein areas of sight are arranged such that opposite surfaces of the object of measurement are scannable.

13. Device in accordance with claim 9, wherein one or several areas of sight is or are externally or internally selectable.

14. Device in accordance with claim 1, wherein the second distance sensor or a second distance sensor combination comprising the second distance sensor and at least one further distance sensor for scanning the object of reference comprises a plurality of areas of sight.

15. Device in accordance with claim 14, wherein the areas of sight are arranged such that an identical surface area of the object of reference is scannable upon linear movement of the second distance sensor or the second distance sensor combination.

16. Device in accordance with claim 14, wherein areas of sight are arranged such that an identical surface area of the object of reference is scannable upon rotational movement of the second distance sensor or the second distance sensor combination.

17. Device in accordance with claim 14, wherein areas of sight are arranged such that opposite surfaces of the object of reference are scannable.

18. Device in accordance with claim 14, wherein one or several areas of sight is or are externally or internally selectable.

19. Device in accordance with claim 1, wherein a distance sensor or a combination of several distance sensors is designed as a probe which is insertable into a bore.

20. Device in accordance with claim 1, wherein object of measurement and object of reference are made of a metallic material.

21. Device in accordance with claim 1, wherein the first distance sensor is an inductive sensor which inductively couples with the object of measurement.

22. Device in accordance with claim 21, wherein an inductive sensor comprises a plurality of coils.

23. Device in accordance with claim 1, wherein the second distance sensor is an inductive sensor which inductively couples with the object of reference.

24. Device in accordance with claim 23, wherein an inductive sensor comprises a plurality of coils.

25. Method for checking bores in or edges on an object of measurement, comprising:

scanning a prepared object of reference with a distance sensor;

scanning the object of measurement in correlation therewith with a further distance sensor for checking bores in or edges on said object of measurement; and comparing the measurement signals of the two distance sensors.

26. Method in accordance with claim 25, wherein the distance sensor and the further distance sensor are of essentially the same design.

27. Method in accordance with claim 25, wherein the distance sensors are inserted like a probe with a respective detector head into the bores of object of reference and object of measurement.

28. Method in accordance with claim 25, wherein a distance sensor comprises a detector head which electromagnetically couples with the object or acts upon the object with a signal and receives a reaction signal from the object, the electromagnetic coupling or the reaction signal being a function of the distance of the detector head from the object.

* * * * *